United States Patent
Hala et al.

(10) Patent No.: US 8,203,350 B2
(45) Date of Patent: Jun. 19, 2012

(54) APPARATUS AND METHOD FOR DIRECT MEASUREMENT OF RECIPROCATING COMPRESSOR RIDER BAND WEAR

(75) Inventors: Roger Aloysius Hala, Gardnerville, NV (US); Brian Francis Howard, Issaquah, WA (US)

(73) Assignee: General Electric Company, Schenectady, NY (US)

( * ) Notice: Subject to any disclaimer, the term of this patent is extended or adjusted under 35 U.S.C. 154(b) by 378 days.

(21) Appl. No.: 12/572,460

(22) Filed: Oct. 2, 2009

(65) Prior Publication Data

US 2011/0080183 A1   Apr. 7, 2011

(51) Int. Cl.
*G01R 27/08* (2006.01)

(52) U.S. Cl. ........................................ 324/699

(58) Field of Classification Search ............... 324/699
See application file for complete search history.

(56) References Cited

U.S. PATENT DOCUMENTS

| | | | |
|---|---|---|---|
| 3,303,988 A * | 2/1967 | Weatherhead | ............ 417/298 |
| 4,987,774 A | 1/1991 | De Waal | |
| 6,318,147 B1 | 11/2001 | Steinruck et al. | |

* cited by examiner

*Primary Examiner* — Thomas Valone
(74) *Attorney, Agent, or Firm* — Hoffman Warnick LLC; Ernest G. Cusick

(57) ABSTRACT

A method and apparatus for direct measurement of rider band wear in a valve assembly for a reciprocating compressor is provided. A distance transducer probe is inserted through a compressor valve assembly to measure a distance between a piston assembly and the transducer probe and the wear of a rider band is determined based on the distance.

18 Claims, 4 Drawing Sheets

APPARATUS AND METHOD FOR DIRECT MEASUREMENT OF RECIPROCATING COMPRESSOR RIDER BAND WEAR

BACKGROUND OF THE INVENTION

The present invention relates generally to reciprocating compressors, and more particularly to a method and apparatus for direct measurement of rider band wear on a reciprocating compressor.

Industrial reciprocating compressors utilize piston rods and distance pieces to separate the process gas from the oil lubricated components in the frame and crosshead guide. The piston rod moves back and forth and requires support on both ends. On one end of the piston rod, the cross head provides support. An oil pump provides pressurized oil to lubricate the crosshead and crosshead guide.

On the other end, rider bands support the piston assembly and rod. Frequently, the process or process gas cannot tolerate oil or only small amounts of lubrication. With low rates of lubrication, the rider band wears quickly, compared to the lubricated components on the other end of the piston rod. The wear rate may not be linear and can be affected by the quality and quantity of oil in the cylinder, process gas composition, process gas debris and other factors.

To accurately measure the gap between the piston and cylinder bore, the operator must stop the machine, purge the cylinder, remove the cylinder head and/or valve assemblies and use feeler gauges to make the measurement.

Methods currently exist for approximating this measurement. For example, using a sensor mounted at the packing case and geometry to extrapolate wear. Another example is mounting a sensor to the piston and using a wireless apparatus to transmit the gap between the piston and cylinder bore outside of the cylinder to a sensor system. Yet another method involves inferring the gap between the piston and cylinder by measuring the gap between a fixture on the piston and a fixture on the cylinder head. However, these methods all require significant modification of the piston and cylinder head.

BRIEF DESCRIPTION OF THE INVENTION

A method and apparatus for direct measurement of rider band wear in a valve assembly for a reciprocating compressor is provided. A distance transducer probe is inserted through a compressor valve assembly to measure a distance between a piston assembly and the transducer probe and the wear of a rider band is determined based on the distance. A computer device can be provided that receives a plurality of distance measurements over time, determines a difference in the measured distances over time; and translates the difference in measured distances over time into an indication of the rider band wear. As such, the wear, i.e., remaining thickness, of a rider band can be determined during normal operation of the compressor.

A first aspect of the invention provides a valve assembly for use in a reciprocating compressor, the valve assembly comprising: a valve cage surrounding a valve in the valve assembly, the valve cage adjacent to a piston assembly, the piston assembly including a piston, a piston rod, and a rider band positioned on the piston; and a distance transducer probe extending through the valve cage, wherein the probe is configured to measure a distance between the piston and the distance transducer probe, the distance being indicative of wear of the rider band.

A second aspect of the invention provides a reciprocating compressor comprising: a piston assembly including a piston, a piston rod, and a rider band positioned on the piston; and a compressor valve assembly including: a valve cage surrounding a valve in the valve assembly, the valve cage adjacent to the piston assembly; and a distance transducer probe extending through the valve cage, wherein the probe is configured to measure a distance between the piston and the distance transducer probe, the distance being indicative of wear of the rider band.

A third aspect of the invention provides a method for direct measurement of rider band wear in a valve assembly for a reciprocating compressor, the method comprising: inserting a distance transducer probe through a valve cage surrounding a valve in the valve assembly such that a tip of the probe is proximate to a piston assembly, the piston assembly including a piston, a piston rod, and a rider band positioned on the piston; using the distance transducer probe to measure a distance between the piston and the distance transducer probe; and determining wear of the rider band based on the distance.

DETAILED DESCRIPTION OF THE INVENTION

Figure 1:
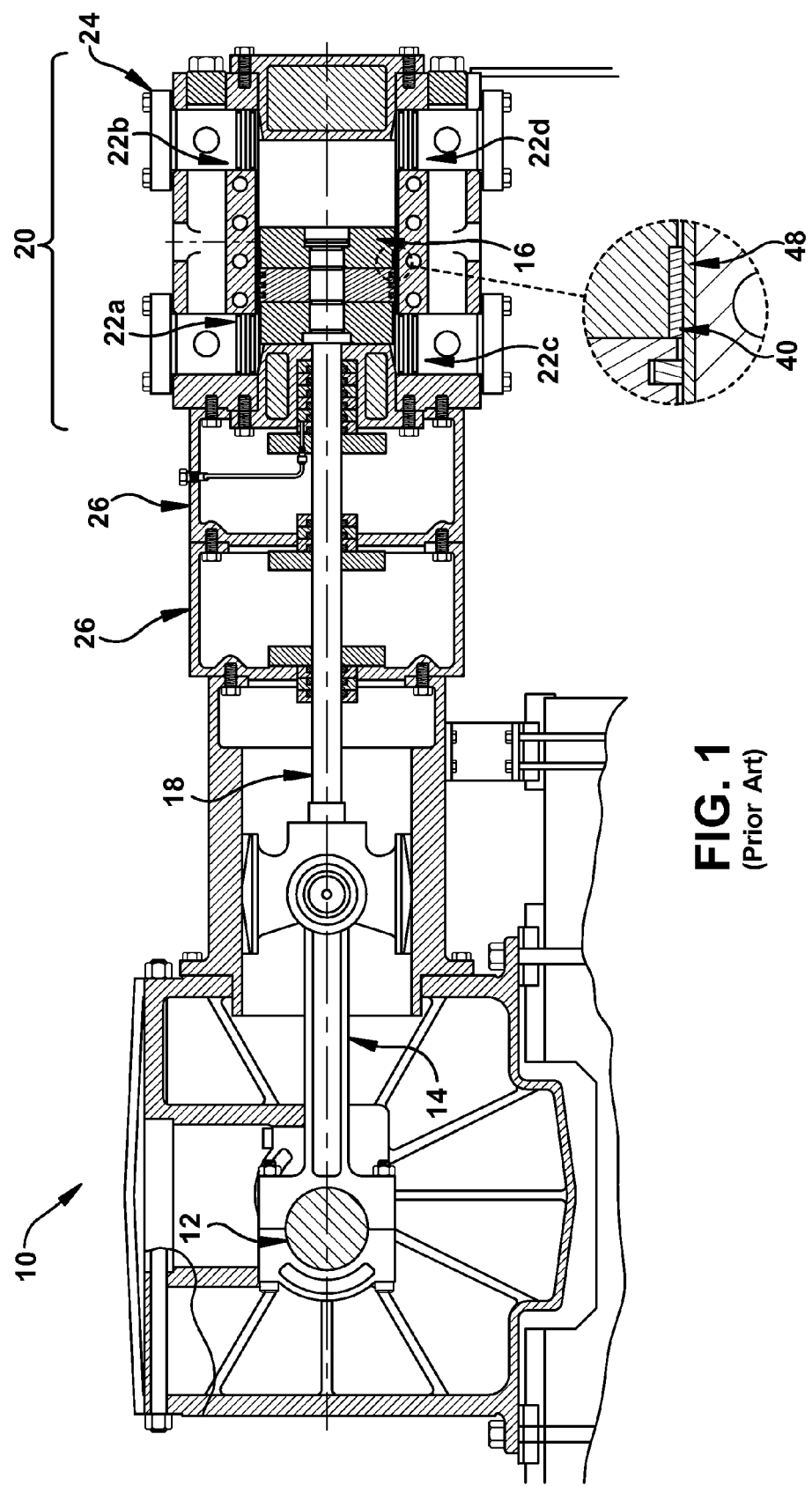
FIG. 1 is a cross-sectional view of a compressor assembly as known in the art.
Figure 2:
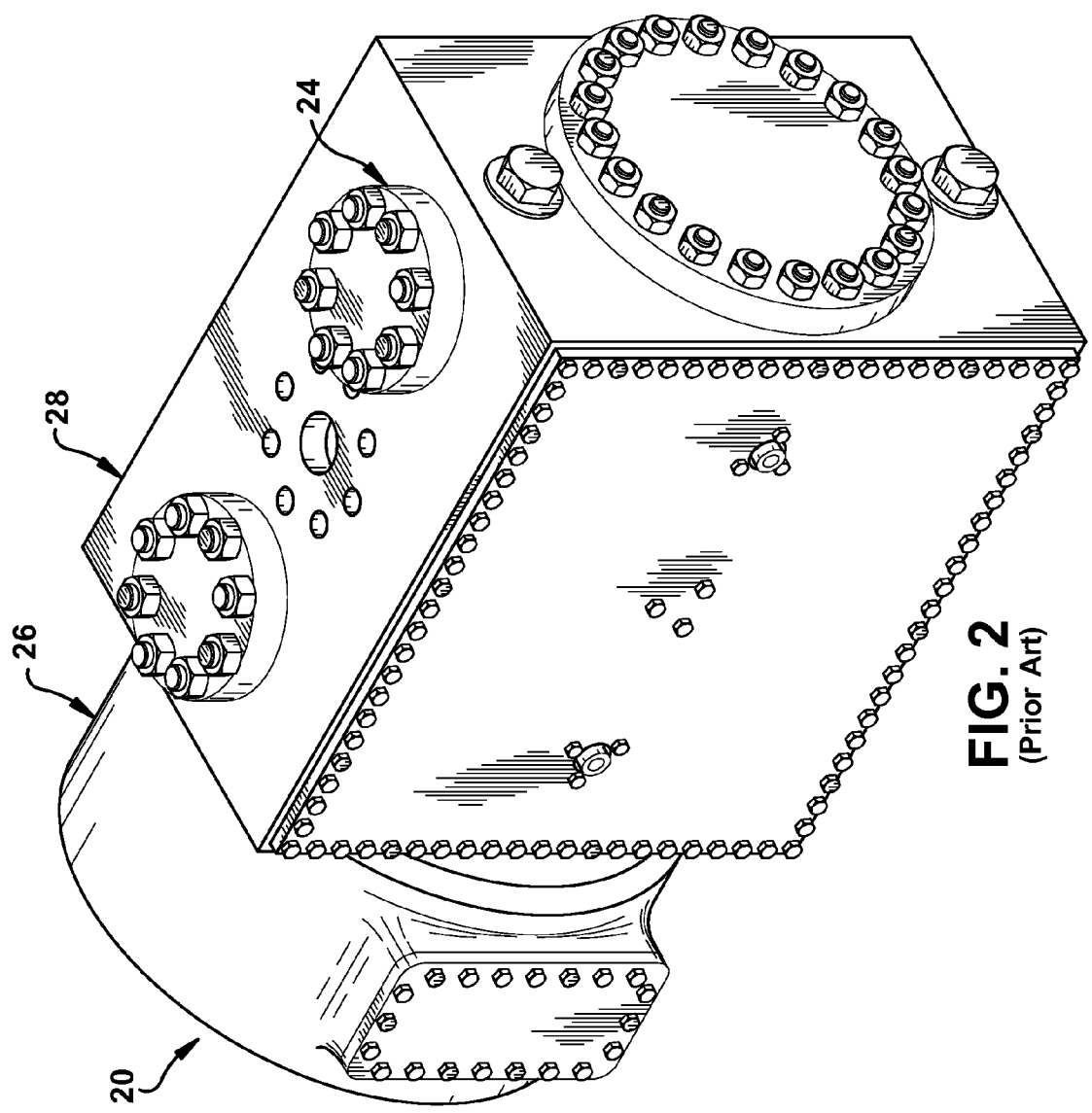
FIG. 2 is a perspective view of a compressor cylinder as known in the art.

Turning to the figures, FIG. 1 shows a cross-sectional view of a reciprocating compressor assembly 10. As known in the art, compressor assembly 10 can include a crank pin 12, a connecting rod 14, and a piston 16 connected to a piston rod 18, wherein piston 16 and piston rod 18 are collectively referred to herein as a piston assembly. Compressor assembly 10 further includes a compressor cylinder 20. Compressor cylinder 20 can include a plurality of cylinder valve assemblies 22a-22d, a plurality of valve covers 24, at least one distance piece 26, and a cylinder liner 48. As shown in FIG. 2, compressor cylinder 20 can further include a cylinder body 28.

As shown in the cross-sectional view in FIG. 1, piston 16 can be configured to over-run cylinder valve assemblies 22a-22d when piston 16 is fully extended (i.e., at top dead center as known in the art) or fully retracted (i.e., at bottom dead center as known in the art). As shown in the exploded portion of FIG. 1, a rider band 40 is included between piston 16 and a cylinder liner 48 of compressor cylinder 20 to support piston 16 and piston rod 18. Rider band 40 can be any size and shape adequate to support piston 16, for example, rider band 40 can be a ring that is loose, mounted in a groove in piston 16, which completely encircles piston 16. As rider band 40 carries the weight of piston 16 and moves against cylinder liner 48, rider band 40 wears and becomes thinner. An embodiment of this invention provides a method and apparatus to directly measure the wear, or remaining thickness, of rider band 40.

Figure 3:
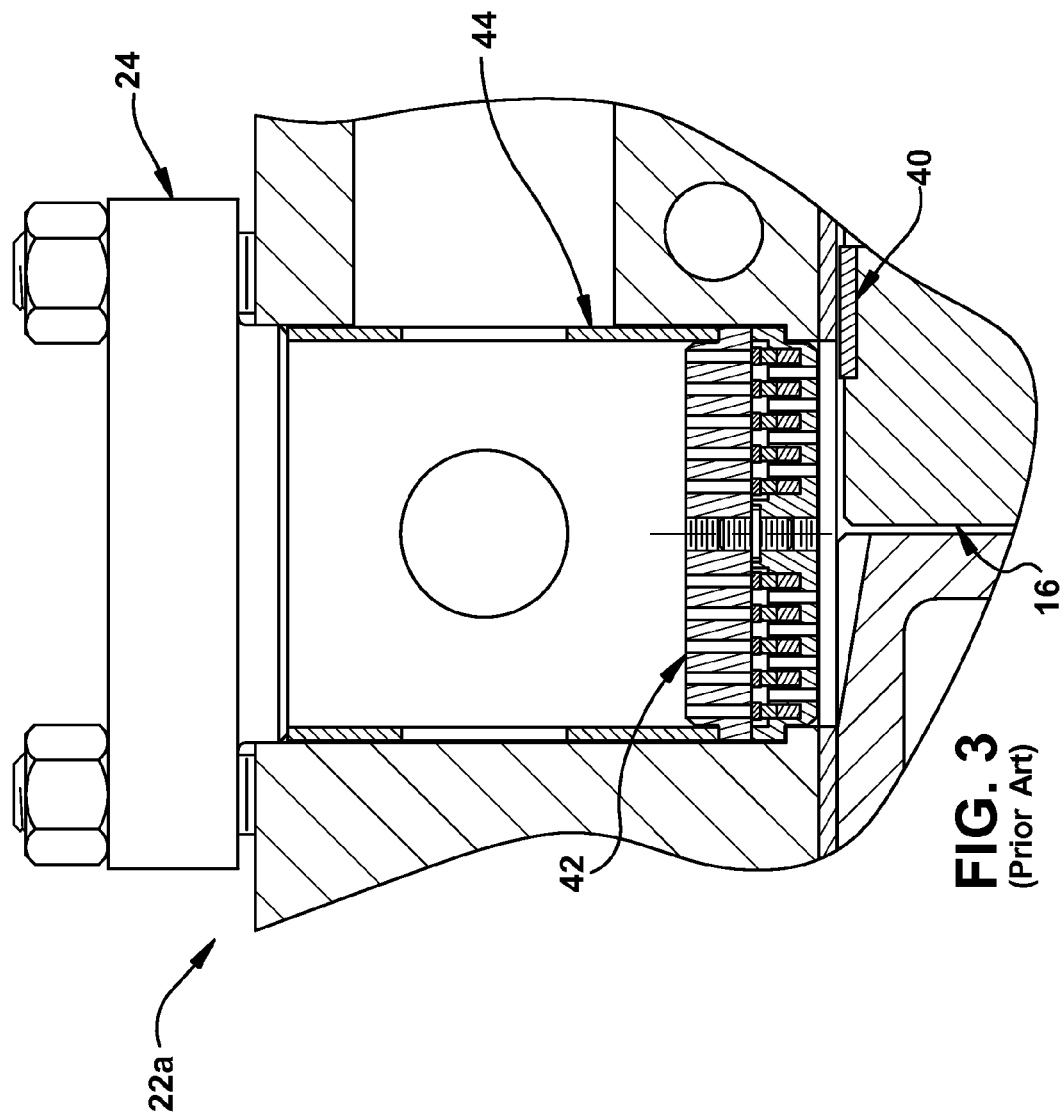
FIG. 3 is a cross-sectional view of a valve assembly as known in the art.

FIG. 3 shows a cross-section of compressor cylinder valve assembly 22a. As shown in FIG. 3, cylinder valve assembly 22a includes a valve 42, a valve cage 44 and valve cover 24 (also shown in FIGS. 1 and 2). As known in the art, valve 42 acts as a check valve allowing gas to flow only in one direction. Specifically, valve 42 acts on valve cage 44 that, in turn, acts on valve 42 to hold it in place. As known in the art, sealing systems, i.e. gaskets, o-rings, etc. (not shown), can be included to seal between valve 42 and cylinder body 28 (FIG. 2) and between valve cover 24 and cylinder body 28 (FIG. 2).

Figure 4:
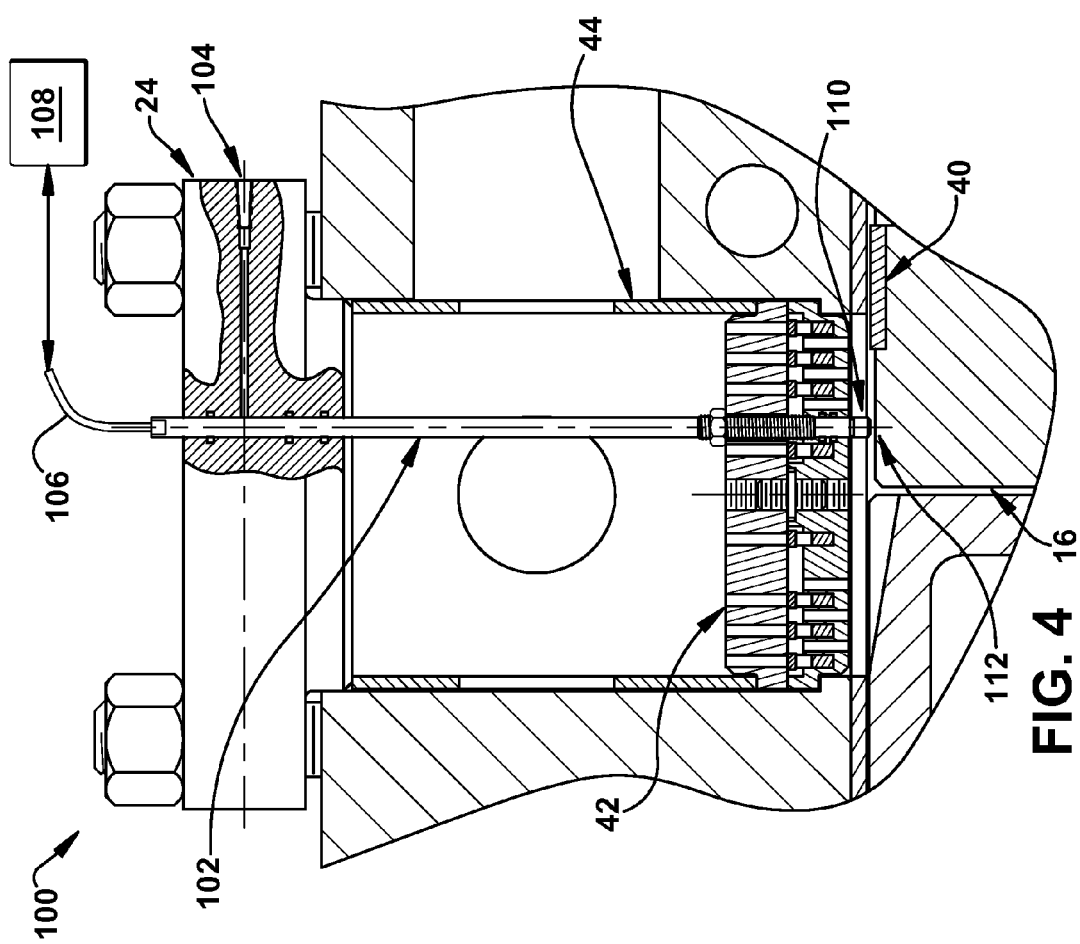
FIG. 4 is a cross-sectional view of a valve assembly according to embodiments of this invention.

Turning to FIG. 4, a cross-sectional view of a valve assembly 100 according to embodiments of this invention is shown. Valve assembly 100 is a modified version of valve assembly 22a shown in FIG. 3. It is understood that while valve assembly 22a is shown for exemplary purposes in FIGS. 3 and 4, any valve assembly (i.e., 22a-22d) could be modified according to embodiments of this invention. An embodiment of this invention provides a method, using valve assembly 100, to directly measure the wear of rider band 40. In one embodiment, a distance transducer probe 102 is inserted through valve assembly 100. For example, transducer probe 102 can be inserted through valve cover 24, and through valve cage 44, so that a tip 110 of transducer probe 102 is outside valve cage 44 and proximate to piston 16. Probe 102 can extend just past valve assembly 100 or could be mounted flush with valve assembly 100.

Valve cover 24 can optionally include a vent 104. If the seals closest to cylinder body 28 (FIG. 2) begin to fail, gases will leak out of vent 104. As such, vent 104 can indicate whether there is a leak within cylinder body 28 (FIG. 2). Transducer probe 102 can be inserted at a substantially 90° angle relative to valve cover 24, or at an angle, i.e., less than or greater than 90° relative to valve cover 24.

Transducer probe 102 is then used to measure a distance between piston 16 and transducer probe 102 over time, and therefore a difference in position can be tracked. Whether this difference in position gets larger or smaller when rider band 40 wears depends on the configuration of cylinder assemblies 22a-22d (FIG. 1) and pistons 16. For example, if cylinder assembly 22c (FIG. 1), with a piston 16 above cylinder assembly 22c (FIG. 1), is modified according to embodiments of this invention, as rider band 40 wears, piston 16 will move closer to cylinder assembly 22c (FIG. 1). However, if cylinder assembly 22a (FIG. 1), where piston 16 is underneath cylinder assembly 22a (FIG. 1), was modified according to embodiments of this invention, then as rider band 40 wears, piston 16 will move farther away from cylinder assembly 22a (FIG. 1). Regardless of whether piston assembly 16 and cylinder assemblies 22a-22d (FIG. 1) (and therefore transducer probe 102) get closer together or farther apart as rider band 40 wears thinner, the wear of rider band 40 can be determined from the difference in position between piston 16 and transducer probe 102 over time, and during normal operation of the compressor.

Transducer probe 102 can be any known type of transducer probe, configured to measure distances between objects in a sensor area, for example, an eddy current transducer. For example, if an eddy current transducer is used, transducer probe 102 can emit an electronic field, the field changing in response to piston 16 being introduced into sensor area 112, i.e., generally the area immediately adjacent to tip 110 of probe 102.

As shown in FIG. 4, valve assembly 100 accepts distance transducer probe 102. Any suitable method of modifying valve assembly 100 to accept transducer probe 102 could be utilized, including boring and machining valve assembly 100 so that probe 102 could be inserted through valve assembly 100. Sealing systems, such as an o-ring, can be used between probe 102 and valve 42 to prevent leakage across probe 102 when valve 42 is closed and sealing systems can be used where probe 102 exits valve cover 24 to prevent gas leakage to the environment. Probe 102 can be inserted into valve cage 44 at any desirable position, for example, probe 102 can be inserted such that it is positioned substantially through a center of valve cage 44, and as such can replace a center bolt (not shown) in valve cage 44 which holds valve assembly 100 together.

An embodiment of this invention can also include a device for continuously or intermittently outputting the results of the measurements from probe 102. In one embodiment, distance transducer probe 102 can include an electrical output 106 to output the distance measurements, and appropriate electronics for converting sensor signals, e.g., electrical output 106, to a form suitable for transmission to an electronic computer device 108.

Electronic computer device 108 can include means for retrieving or receiving data from probe 102, i.e., the distance measurements, as well as the capacity (such as through a database) to store and retrieve historical data. Electronic computer device 108 can further be equipped with program code for translating the distance measurement data from probe 102 into an indication of the wear of rider band 40. For example, a lookup table or other similar means of corresponding the distance measurement data with wear of rider band 40 can be provided. In addition, program code can be provided that uses an algorithm or lookup table to translate the measurement data into a value indicative of the wear of rider band 40. Electronic computer device 108 can further be equipped with a display and with software suitable for drawing plots from the present or historical data. An electronic computer communication network can also be provided to link the various electronic components.

The terms "first," "second," and the like, herein do not denote any order, quantity, or importance, but rather are used to distinguish one element from another, and the terms "a" and "an" herein do not denote a limitation of quantity, but rather denote the presence of at least one of the referenced item. The modifier "about" used in connection with a quantity is inclusive of the stated value and has the meaning dictated by the context, (e.g., includes the degree of error associated with measurement of the particular quantity).

While the disclosure has been particularly shown and described in conjunction with a preferred embodiment thereof, it will be appreciated that variations and modifications will occur to those skilled in the art. Therefore, it is to be understood that the appended claims are intended to cover all such modifications and changes as fall within the true spirit of the disclosure.

What is claimed is:

1. A valve assembly for use in a reciprocating compressor, the valve assembly comprising:
 a valve cage surrounding a valve in the valve assembly, the valve cage adjacent to a piston assembly, the piston assembly including a piston, a piston rod, and a rider band positioned on the piston; and
 a distance transducer probe extending through a valve cover into the valve cage, wherein the probe is configured to measure a distance between the piston and the distance transducer probe, the distance being indicative of wear of the rider band.

2. The valve assembly of claim 1, wherein the distance transducer probe is further configured to output the distance measurement in the form of an electrical signal.

3. The valve assembly of claim 2, further comprising a computer device configured to:
 receive a plurality of distance measurements over time;
 determine a difference in the measured distances over time; and
 translate the difference in measured distances over time into an indication of the rider band wear.

4. The valve assembly of claim 3, further including an outputting device configured to output an electrical output indicative of the wear of the rider band.

5. The valve assembly of claim 1, wherein the distance transducer probe is an eddy current transducer which emits an electronic field, the field changing in response to the piston assembly being introduced into a sensor area, and measures the distance between the piston and distance transducer probe based on the change in the electronic field.

6. The valve assembly of claim 1, wherein the distance transducer probe extends through substantially a center of the valve cage.

7. The valve assembly of claim 1, wherein the valve cover includes a vent.

8. The valve assembly of claim 1, wherein the distance transducer probe extends through the valve cover at a substantially 90° angle relative to the valve cover.

9. A reciprocating compressor comprising:
a piston assembly including a piston, a piston rod, and a rider band positioned on the piston; and
a compressor valve assembly including:
a valve cage surrounding a valve in the valve assembly, the valve cage adjacent to the piston assembly; and
a distance transducer probe extending through a valve cover into the valve cage, wherein the probe is configured to measure a distance between the piston and the distance transducer probe, the distance being indicative of wear of the rider band.

10. The reciprocating compressor of claim 9, wherein the distance transducer probe is further configured to output the distance measurement in the form of an electrical signal.

11. The reciprocating compressor of claim 10, further comprising a computer device configured to:
receive a plurality of distance measurements over time;
determine a difference in the measured distances over time; and
translate the difference in measured distances over time into an indication of the rider band wear.

12. The reciprocating compressor of claim 11, further including an outputting device configured to output an electrical output indicative of the wear of the rider band.

13. The reciprocating compressor of claim 9, wherein the distance transducer probe is an eddy current transducer which emits an electronic field, the field changing in response to the piston assembly being introduced into a sensor area, and measures the distance between the piston and distance transducer probe based on the change in the electronic field.

14. The reciprocating compressor of claim 9, wherein the distance transducer probe extends through the valve cover at a substantially 90° angle relative to the valve cover.

15. A method for direct measurement of rider band wear in a valve assembly for a reciprocating compressor, the method comprising:
inserting a distance transducer probe through a valve cover into a valve cage surrounding a valve in the valve assembly such that a tip of the probe is proximate to a piston assembly, the piston assembly including a piston, a piston rod, and a rider band positioned on the piston;
using the distance transducer probe to measure a distance between the piston and the distance transducer probe; and
determining wear of the rider band based on the distance.

16. The method of claim 15, wherein the distance transducer probe outputs the distance measurement in the form of an electrical signal.

17. The method of claim 16, wherein the determining further comprises:
receiving, on a computer device, a plurality of distance measurements over time;
determining a difference in the measured distances over time; and
translating the difference in measured distances over time into an indication of the rider band wear.

18. The method of claim 17, further comprising outputting an electrical output indicative of the wear of the rider band.

* * * * *